(12) United States Patent
Dore

(10) Patent No.: US 10,888,903 B2
(45) Date of Patent: Jan. 12, 2021

(54) WASHING APPARATUS FOR 3D-PRINTED ARTICLES

(71) Applicant: Quill International Group Limited, Melbourne (GB)

(72) Inventor: David James Dore, Melbourne (GB)

( * ) Notice: Subject to any disclaimer, the term of this patent is extended or adjusted under 35 U.S.C. 154(b) by 144 days.

(21) Appl. No.: 16/329,492

(22) PCT Filed: Sep. 7, 2017

(86) PCT No.: PCT/GB2017/000128
§ 371 (c)(1),
(2) Date: Feb. 28, 2019

(87) PCT Pub. No.: WO2018/046878
PCT Pub. Date: Mar. 15, 2018

(65) Prior Publication Data
US 2019/0184432 A1    Jun. 20, 2019

(30) Foreign Application Priority Data

Sep. 9, 2016 (GB) .................................. 1615321.5

(51) Int. Cl.
*B08B 3/02*         (2006.01)
*B08B 3/14*         (2006.01)
(Continued)

(52) U.S. Cl.
CPC    *B08B 3/02* (2013.01); *A61L 2/10* (2013.01); *B01D 29/27* (2013.01); *B01D 29/90* (2013.01);
(Continued)

(58) Field of Classification Search
None
See application file for complete search history.

(56) References Cited

U.S. PATENT DOCUMENTS

| 4,433,698 A | 2/1984 | Blaul |
| 6,199,565 B1 | 3/2001 | Bluestone |
| 2005/0268949 A1* | 12/2005 | Rosa ........................ B08B 3/14 |
| | | 134/111 |

FOREIGN PATENT DOCUMENTS

| EP | 0852161 A2 | 7/1998 |
| EP | 1982775 A1 | 10/2008 |

(Continued)

OTHER PUBLICATIONS

International Search Report for PCT/GB2017/000128.
International Preliminary Report on Patentability for PPCT/GB2017/000128.

*Primary Examiner* — Michael E Barr
*Assistant Examiner* — Jason P Riggleman
(74) *Attorney, Agent, or Firm* — Egbert Law Offices, PLLC

(57) ABSTRACT

A washing apparatus for a 3D-printed article is provided for the removal of support material from the article. The apparatus includes a glove isolation cabinet with a liquid-discharging nozzle to enable an operator to spray an article with a washing liquid, and a drain. A first filter arrangement receives liquid discharged from the cabinet. The washing liquid drains through the first filter arrangement under the influence of gravity but the first filter arrangement is located in a trough in which washing liquid that has passed through the first filter arrangement accumulates whereby, in use, one or more filters of the first filter arrangement are submerged to ensure filtered-out residue remains submerged in the washing liquid. A pump is provided to pump liquid that has passed through the first filter arrangement through a second filter arrangement adapted to filter out solid material equal to or greater than 5 μm in size.

15 Claims, 10 Drawing Sheets

(51) Int. Cl.
    *B08B 3/00*     (2006.01)
    *B08B 15/02*     (2006.01)
    *B33Y 40/00*     (2020.01)
    *B29C 64/35*     (2017.01)
    *A61L 2/10*     (2006.01)
    *B01D 29/27*     (2006.01)
    *B01D 29/90*     (2006.01)
    *B01D 35/02*     (2006.01)
    *B01D 39/08*     (2006.01)
    *B22F 3/105*     (2006.01)

(52) U.S. Cl.
    CPC ............ *B01D 35/02* (2013.01); *B01D 39/083* (2013.01); *B08B 3/006* (2013.01); *B08B 3/14* (2013.01); *B08B 15/026* (2013.01); *B29C 64/35* (2017.08); *B33Y 40/00* (2014.12); *A61L 2202/11* (2013.01); *A61L 2202/17* (2013.01); *B01D 2239/0208* (2013.01); *B01D 2239/0613* (2013.01); *B22F 3/1055* (2013.01); *B22F 2003/1059* (2013.01)

(56) References Cited

FOREIGN PATENT DOCUMENTS

| | | | |
|---|---|---|---|
| FR | 2452952 | A1 | 10/1980 |
| WO | 2012024729 | A1 | 3/2012 |
| WO | WO2012/024729 | A1 * | 3/2012 |

* cited by examiner

WASHING APPARATUS FOR 3D-PRINTED ARTICLES

The present invention relates to a washing apparatus that is primarily for use in washing articles made by additive manufacturing, commonly called 3D-printing.

3D-printed articles may be made by several additive layer processes but those made by selective laser melting (SML) or by selective laser sintering (SLS), in particular, both use very fine, typically metal, powders to create a solid structure. These structures may have to be cut off a base plate on which they have been formed as the printing process fuses the article to the plate. This is done by wire burning or a similar process but great care has to be taken to avoid sparking as this may ignite loose metal powder on or in the article that remains after the printing process. Such articles may therefore be cleaned along with the base plate to remove this powder prior to removal from the base plate. Even if the article is removed from the base plate prior to cleaning it is still necessary to remove loose powder from the interstices of the printed article. Various techniques have been tried to accomplish this, for example dry ultrasonic vibration has been used. However, this has the disadvantage that shaking the printed article and metal powders it contains creates static that is an explosion risk. Static charges also tend to retain the powder in any interstices within the article so that the process is inefficient. It also discharges the metal powders into the atmosphere, which is a considerable health hazard. Ultrasonic washing of the article in a bath has also been tried but jetting the article with a high-powered jet of a washing liquid such as water has been found to be one of the more effective methods of removing the loose powder. However, typical articles made by SML and SLS techniques may be heavy, for example up to 150 kg, and their weight, particularly if combined with that of a base plate, makes the articles difficult to handle and manipulate in a conventional washing apparatus. Also, the washed out metal powders cannot be simply washed down the drain as they cause pollution but in any event as they are typically expensive heavy metal powders it is desirable to recover them for reuse. Further, metal powders from such articles that become airborne are extremely hazardous being both potentially explosive owing to a build-up or electrical static and a health risk if breathed in by operatives. It is therefore extremely important, therefore, that all particles are trapped and safely contained so that they do not contaminate the environment around a washing apparatus.

Washing apparatus is known, for example as described in EP0852161 comprising an enclosed washing compartment that contains a washing liquid and washed-off residues within it so that the latter do not contaminate the local environment. However, here the washing liquid is simply filtered and collected for reuse and there is no attempt to ensure filter-out residues are not allowed to become airborne when the apparatus is in use or opened up thereafter.

An object of the present invention is to provide a washing apparatus for 3D-printed articles which overcomes or substantially mitigates the aforementioned problems.

According to the present invention there is provided a washing apparatus for a 3D-printed article for removing support material from the article comprising a glove isolation cabinet provided with a liquid-discharging nozzle to enable an operator to spray an article located in the cabinet with a washing liquid and a drain; a first filter arrangement that receives washing liquid discharged from the cabinet via the drain and through which the washing liquid drains under the influence of gravity; a first pump; and a second filter arrangement comprising at least one filter cartridge through which liquid that has passed through the first filter arrangement is pumped by the first pump; characterised in that the first filter arrangement is located in a trough in which washing liquid that has passed through the first filter arrangement accumulates whereby, in use, one or more filters of the filter arrangement are submerged to ensure filtered-out residue remains submerged in the washing liquid.

Keeping the first filter arrangement submerged is important as it ensures that the filtered-out residue cannot become airborne, even when the washing apparatus is opened to remove the washed article and to replace removable filters.

Preferably, a platform is provided within the glove isolation cabinet on which an article to be washed is located, the platform comprising a tray above which is mounted a support plate on which the article sits. Advantageously, the tray comprises a flat plate with a raised edge forming a weir over which the washing liquid cascades but which predominantly retains solid particles in the tray. The flat plate of the tray is preferably covered by a mat. This mat also traps particular residues that are submerged in liquid retained in the tray.

Other preferred but non-essential features of the aspects of the present invention are described in the dependent claims appended hereto.

The present invention will now be described by way of example with reference to the accompanying drawing in which:—

Figure 1:
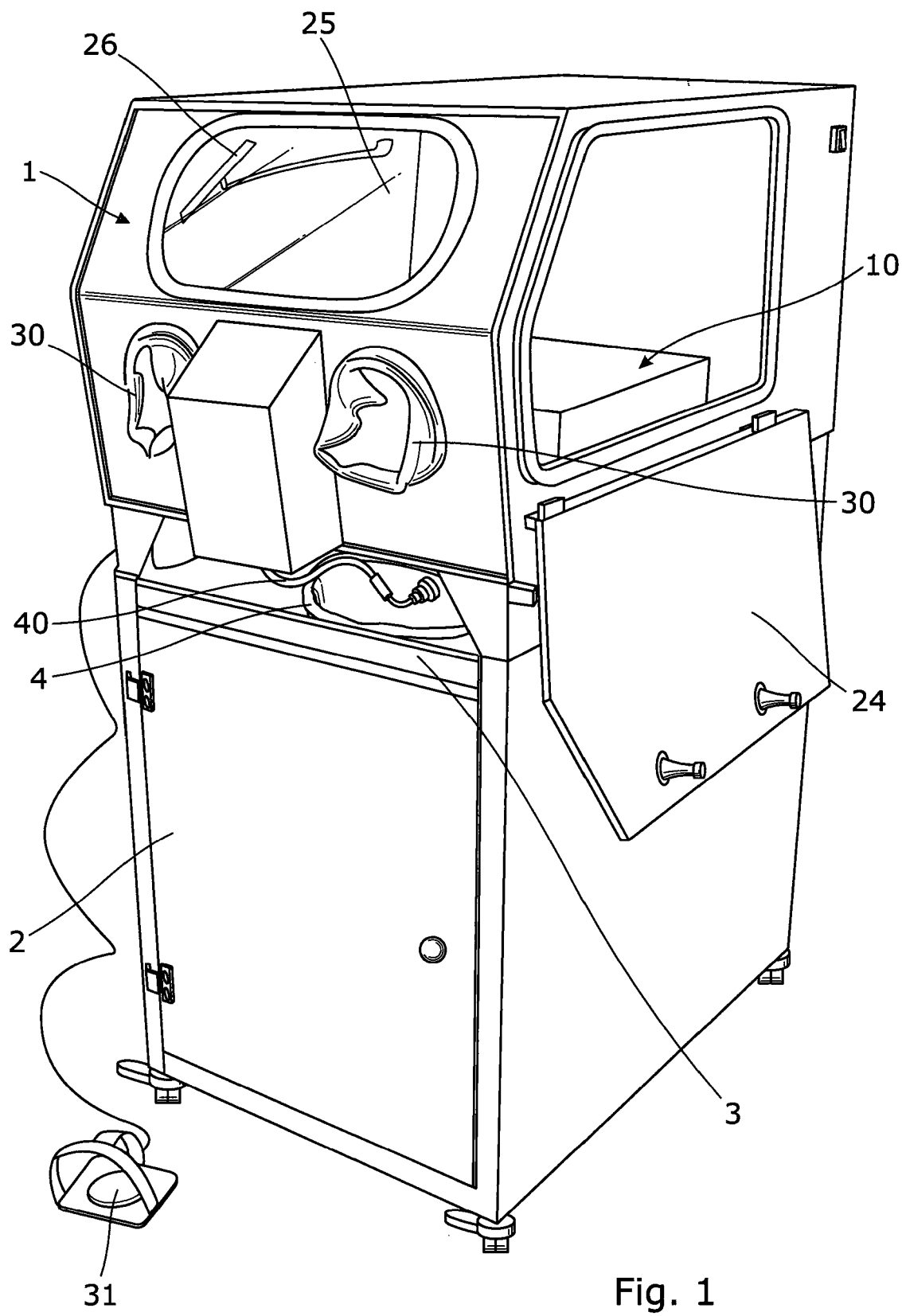
FIG. 1 is a perspective view of a washing apparatus in accordance with the present invention.

An embodiment of washing apparatus for washing 3D-printed articles is shown in FIGS. 1 to 6 and comprises a glove isolation cabinet 1 in which the articles are washed and a washing liquid collection arrangement, which is housed in a cupboard 2 on which the cabinet 1 sits. In the upper part of the cupboard 2 is a trough in the form of a drawer 3 that houses a first filter arrangement 4 through which used washing liquid drains under the influence of gravity In the lower part of the cupboard 2 is a second filter arrangement 5, through which washing liquid that has passed through the first filter arrangement is pumped, and a tank 6 for collecting the washing liquid, which is typically water or deionized water. At the rear of the cabinet 2 is a compartment 7 containing several electrically powered components of the apparatus 1. These may be powered by either a mains electricity supply or by a 12 volt battery 8 that is housed in the compartment 7. A main power on/off switch 9 is provided on the exterior of the apparatus to supply power to the electrically-powered components of the apparatus or to isolate them from the supply. These electrical components and various other components of the apparatus 1 are described in more detail below.

An embodiment of platform 10 for use inside the cabinet 1 is shown in FIGS. 7 to 10. The platform 10 is intended to support an article A (see FIG. 2) to be washed within the cabinet 1. The platform 10 is also designed to be used to transport heavy 3-D printed articles via a lifting vehicle from a build machine to the washing apparatus, the lifting vehicle being adapted to load the platform 10 and the article directly into the cabinet 1. For this purpose the apparatus may be provided with height adjustable legs or castors to enable part of the lifting vehicle to fit beneath it during loading of the cabinet 1.

Preferably, the platform 10 is fabricated from stainless steel so that it is unaffected by the washing liquid, which is typically water. Similarly the interior of the cabinet 1 is also preferably also lined with stainless steel sheets. The construction of the platform 10 will now be described in more detail.

The platform 10 preferably has a rectangular footprint and is of a size such that it can be readily located within and removed from the washing cabinet 2 as required. However, it will be appreciated that it can be made with any appropriate footprint and, in particular, it may be adapted for the particular shape of the 3D-articles to be washed. The platform 10 comprises a rectangular tray 11 above which is mounted a rectangular support plate 12 for the article A by means of a frame 13 that sits on the tray 11. The plate 12 is provided with dependent flanges 14 on all sides and fits snugly into the frame 13, which is also rectangular and has a centrally located cross-bar 15 that supports and underpins the support plate 12. When the support plate 12 is seated on the cross-bar 15 three sides of the frame 14 project above it to form upstands 16 on these three sides. The fourth side of the plate 13 is also provided with an upstand by means of a separate, detachable plate 17 that sits on projections 18 provided in the adjacent flange 19 of the support plate 12. Detachment of the plate 17 enables a heavy article A to be slid on to and off the support plate 12 without it having to be lifted over the upstands 16 or the plate 17.

A plurality of rollers 20 are mounted in the plate 12. These are preferably arranged in a regular pattern, such as a grid, so that an article sitting on the plate 12 is movable over the whole of the surface of the plate 12. Preferably, therefore, the rollers 20 comprise ball bearings rather than cylindrical rollers so that the article can be moved in any direction. The support plate 12 also defines at least one perforation 21 but preferably there is a plurality of slot-like perforations 21 spaced across the width of the plate 12. In use, the perforations 21 enable washing liquid to drain from the plate 12 into the tray 11. The tray 11 comprises a plate 22 with a raised edge 23, which forms a weir over which washing liquid collected in the tray 11 can cascade but which is intended predominantly to retain solid material such as loose powder in the tray 11. Preferably, in use the plate 22 is covered by a removable mat that traps the solid material. It will also be appreciated that this solid material is submerged by liquid retained in the tray 11 by its raised edge.

Figure 2:
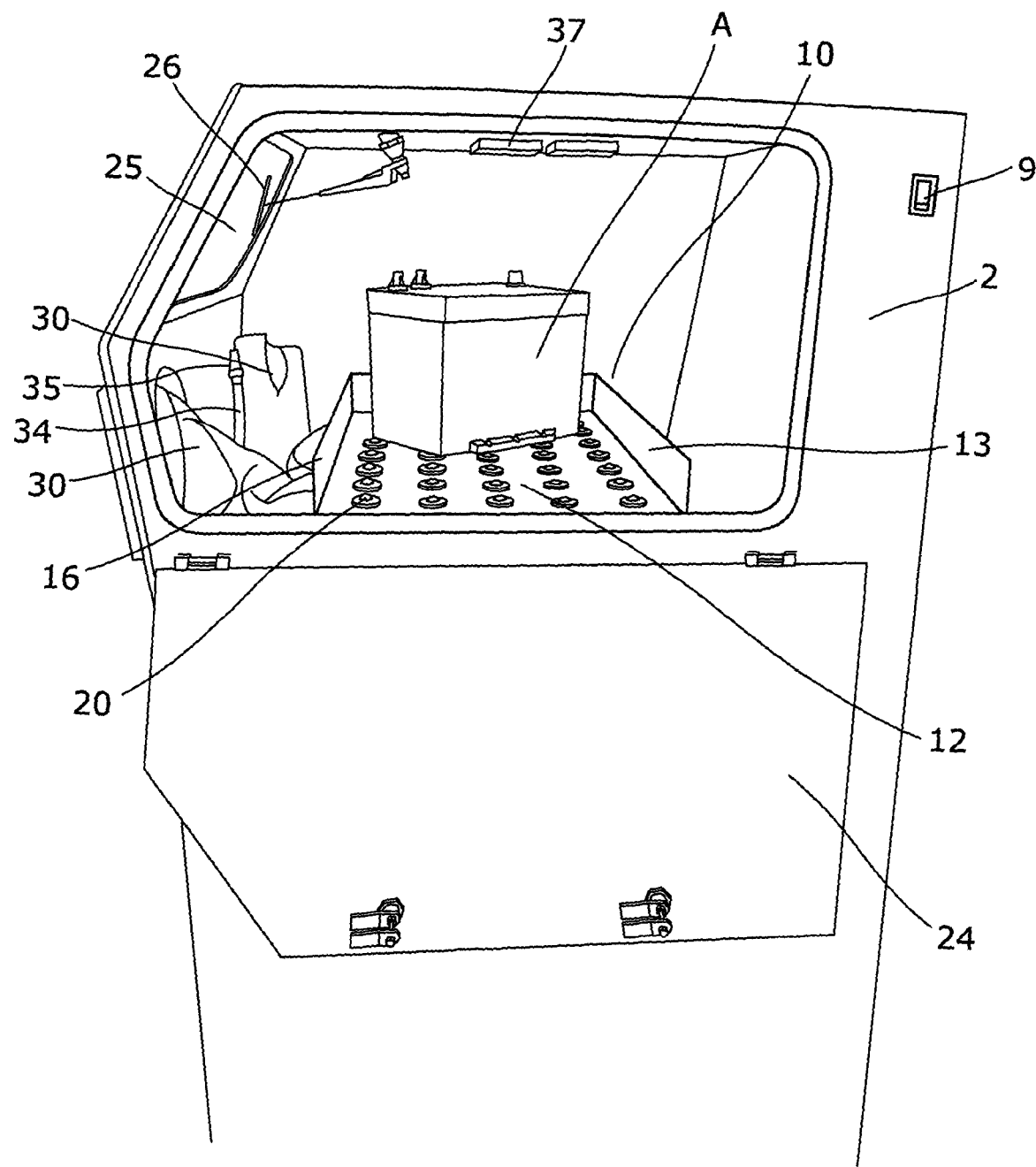
FIG. 2 is a perspective view of the interior of a glove isolation cabinet forming part of the apparatus shown in FIG. 1 and showing the location of a removable platform therein.
Figure 3:
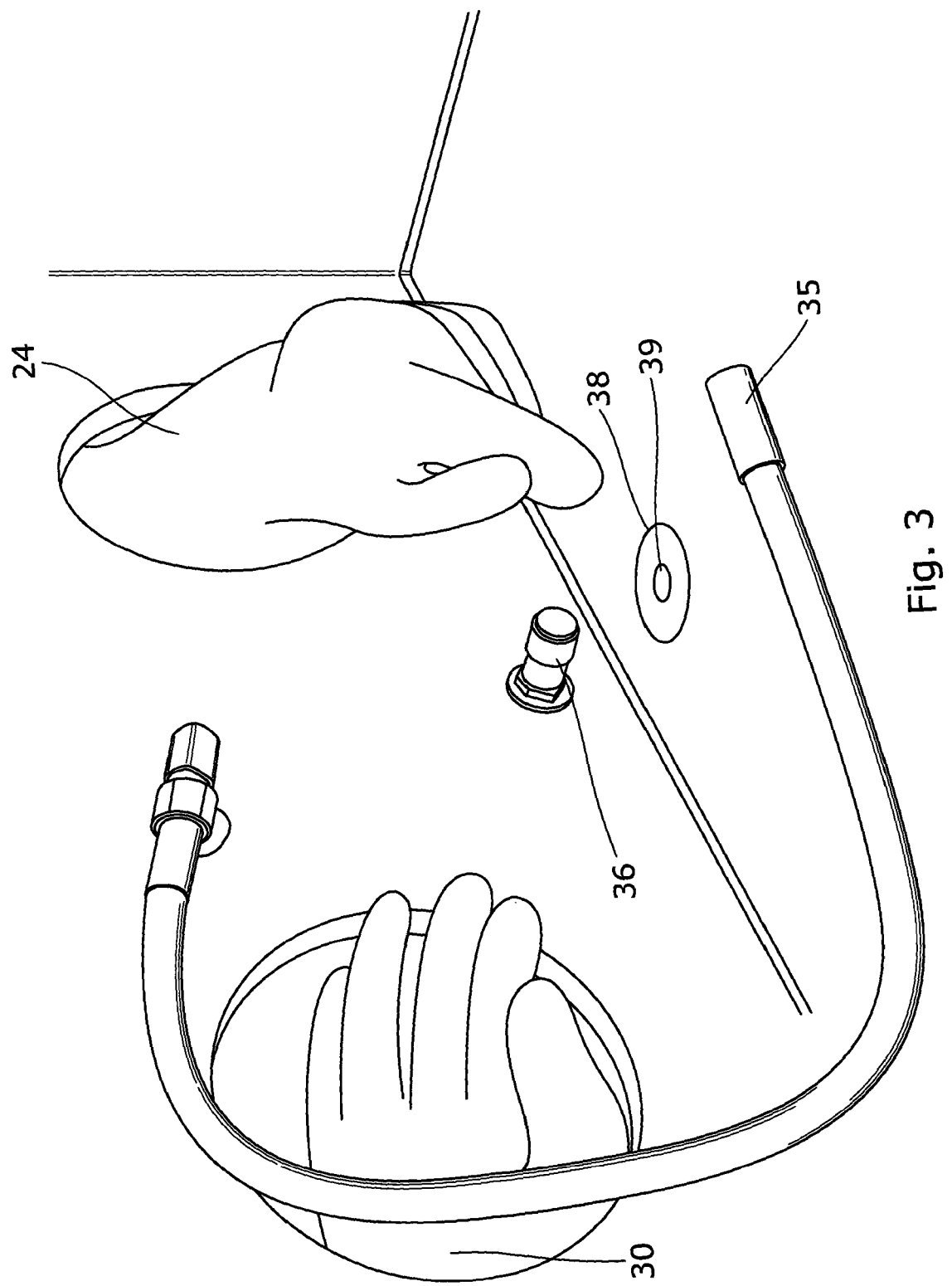
FIG. 3 is a view showing in greater detail and to an enlarged scale part of the interior of the glove isolation cabinet shown in FIG. 2.
Figure 4:
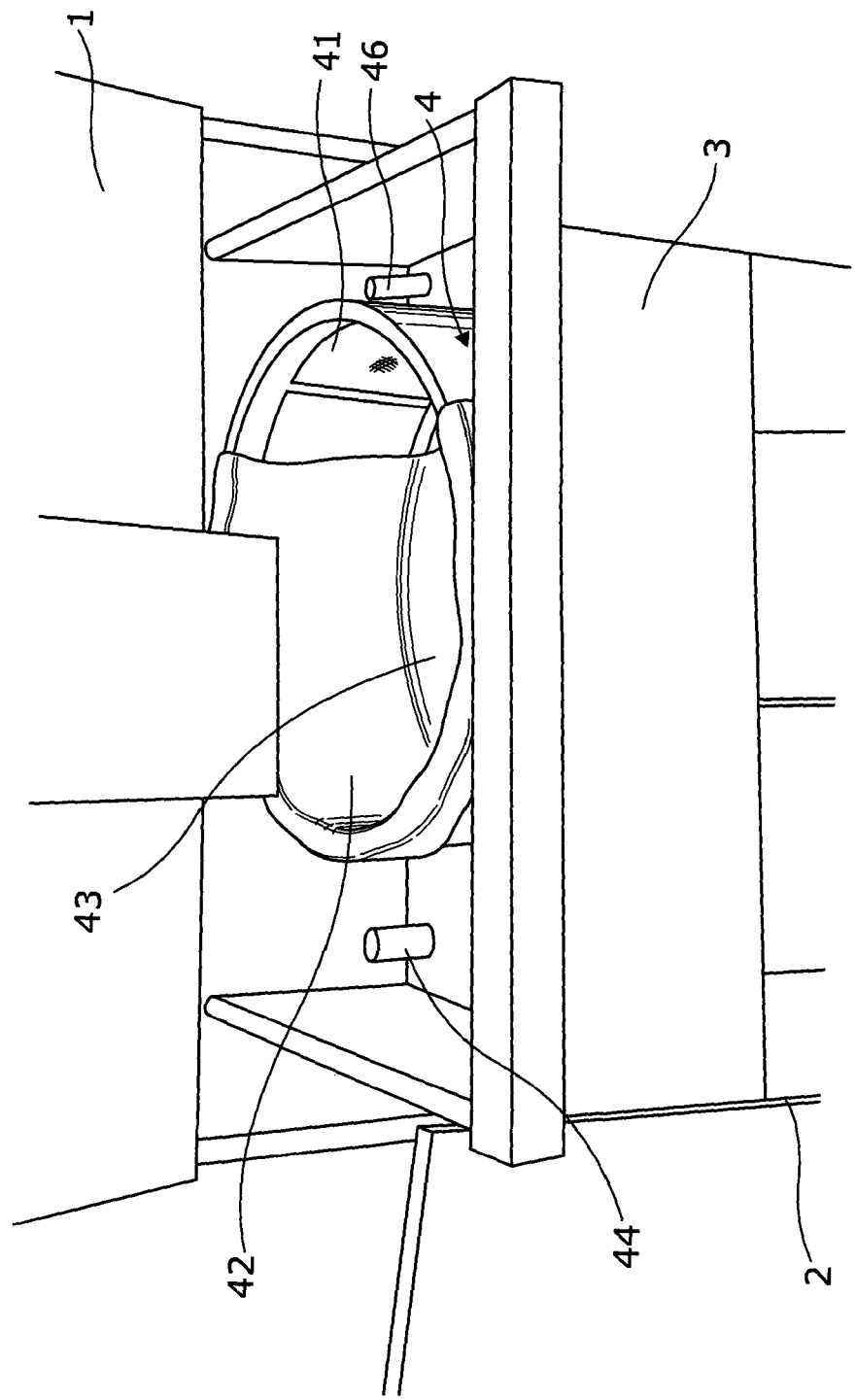
FIG. 4 is a perspective view of the interior of a filtration drawer forming part of the washing apparatus shown in FIG. 1 when pulled partially out of the apparatus and with a removable filter shown partially pulled back to reveal a filter basket beneath.
Figure 5:
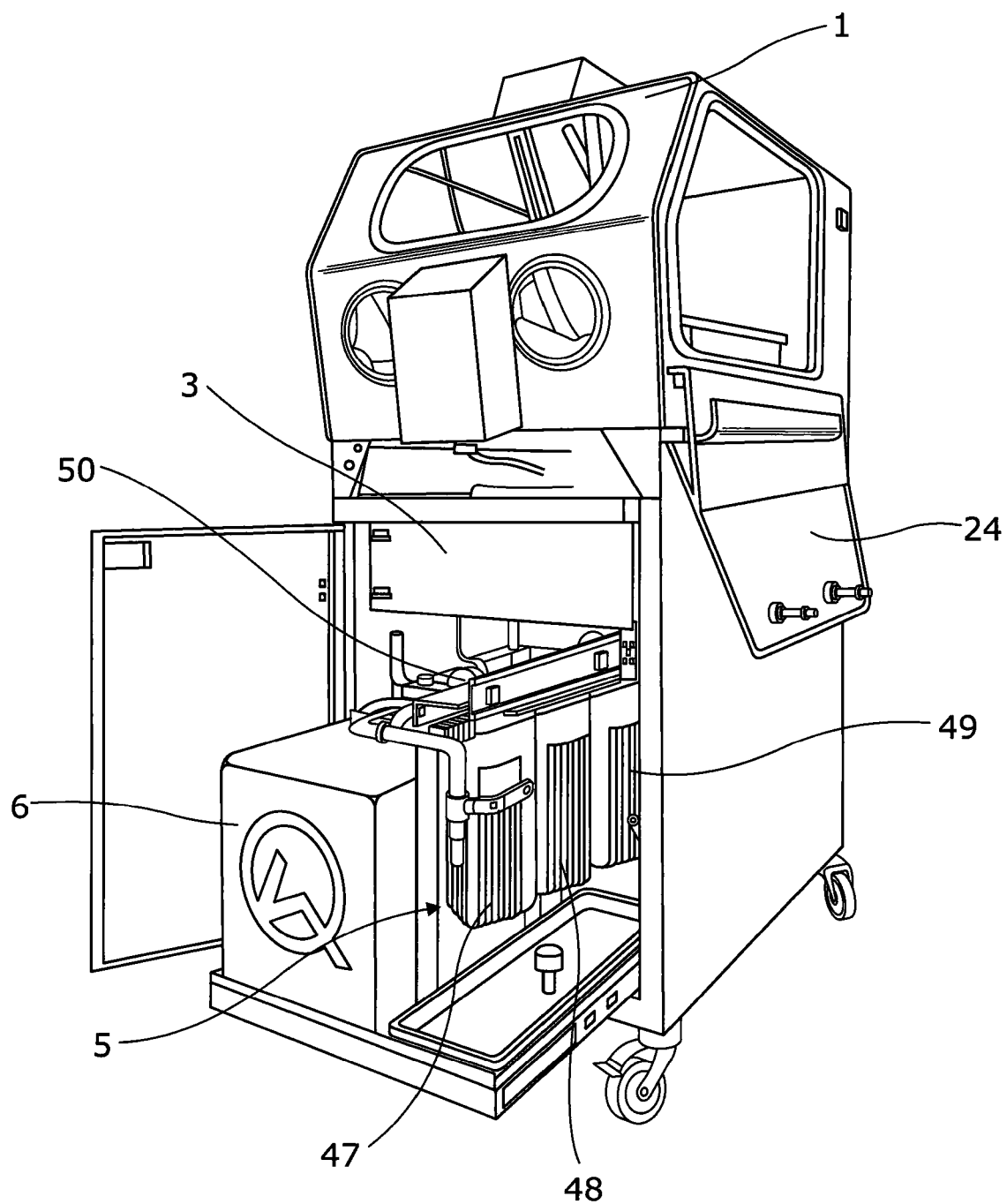
FIG. 5 is a perspective view of the interior of a lower cupboard of the washing apparatus with the contents pulled out on a tray.
Figure 6:
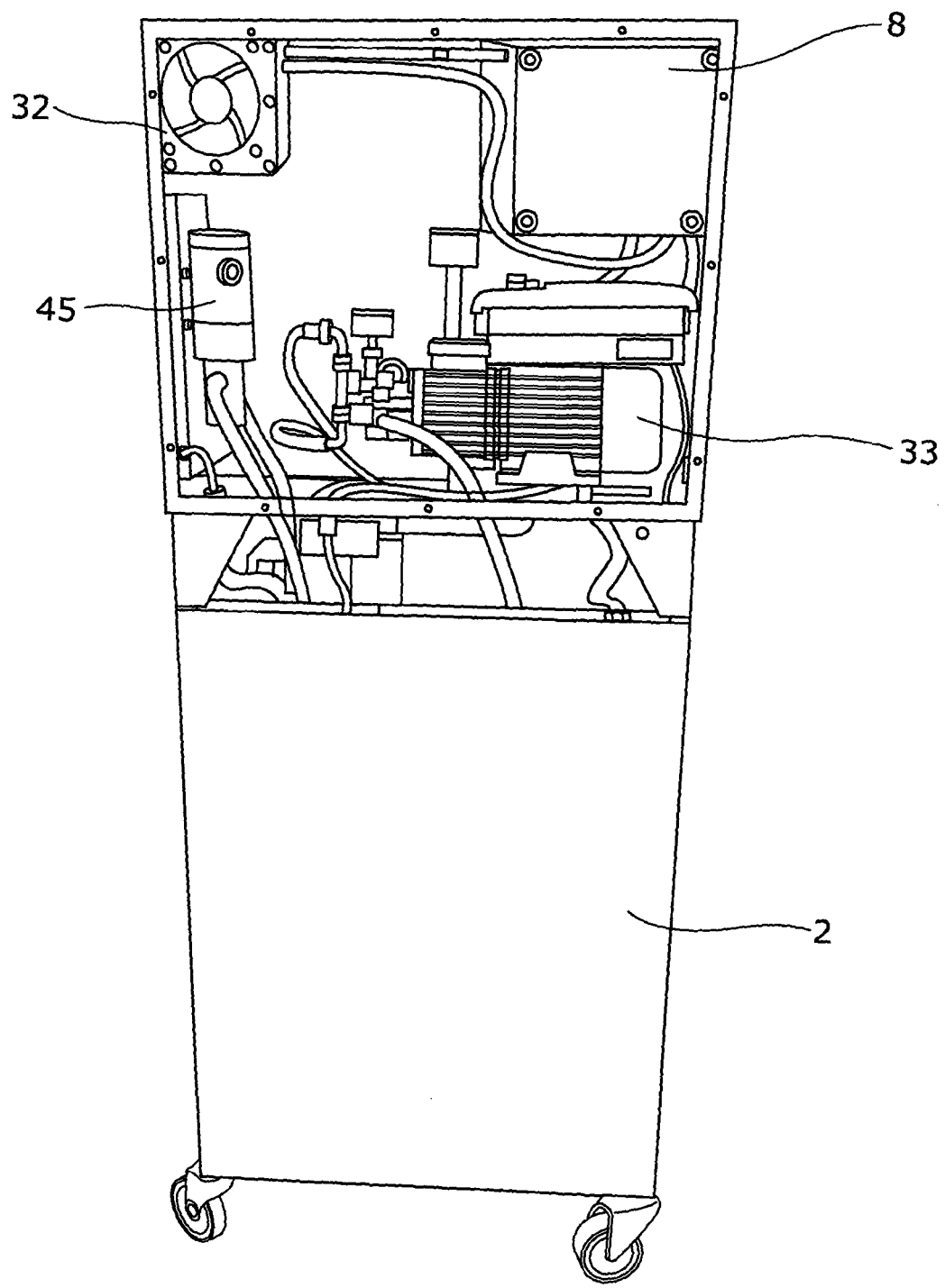
FIG. 6 is a view of the rear of the washing apparatus shown in FIG. 1 with a panel removed to show the interior of a compartment behind the glove isolation cabinet.
Figure 7:
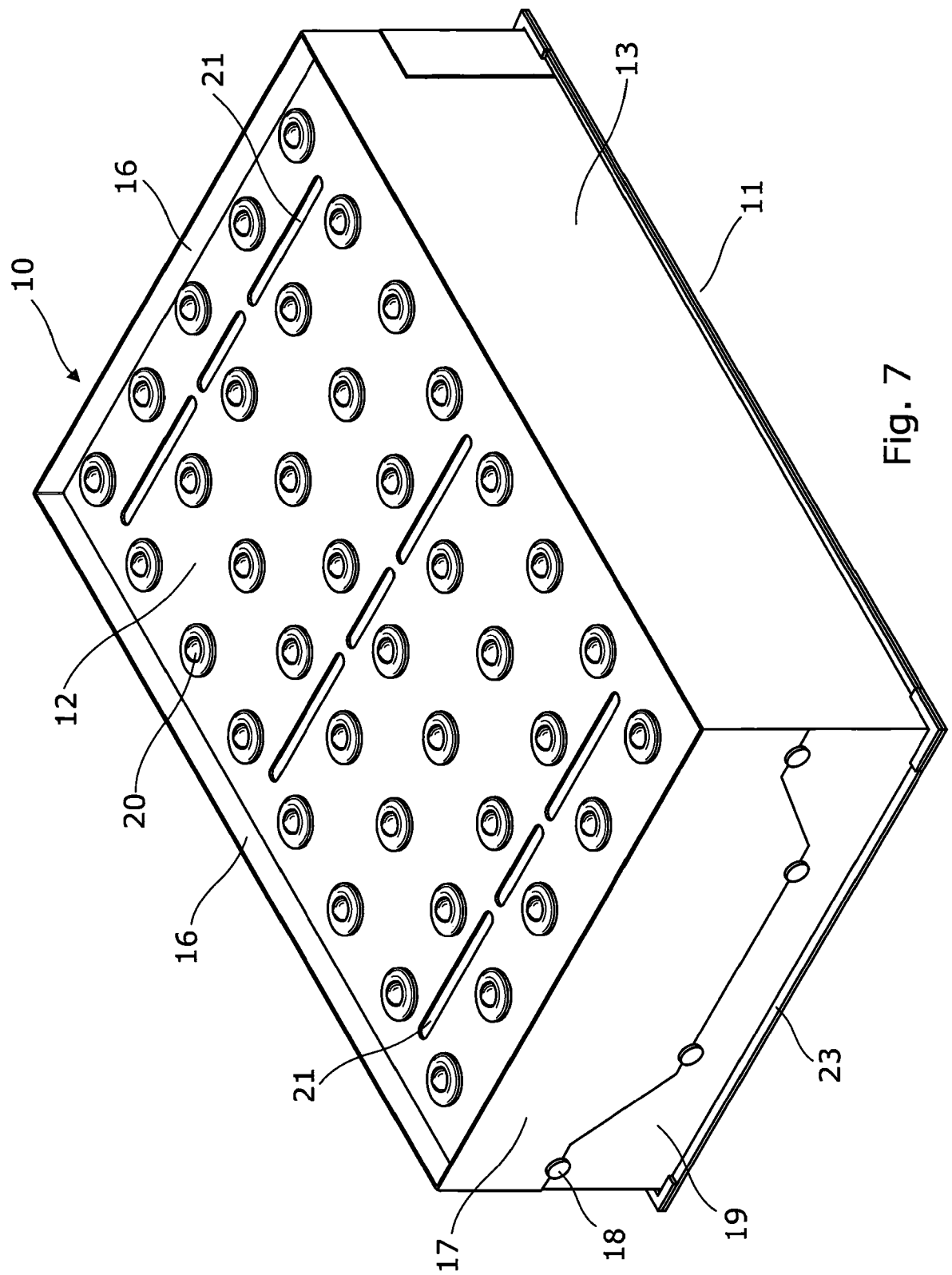
FIG. 7 is a perspective view of the platform shown in FIG. 2.
Figure 8:
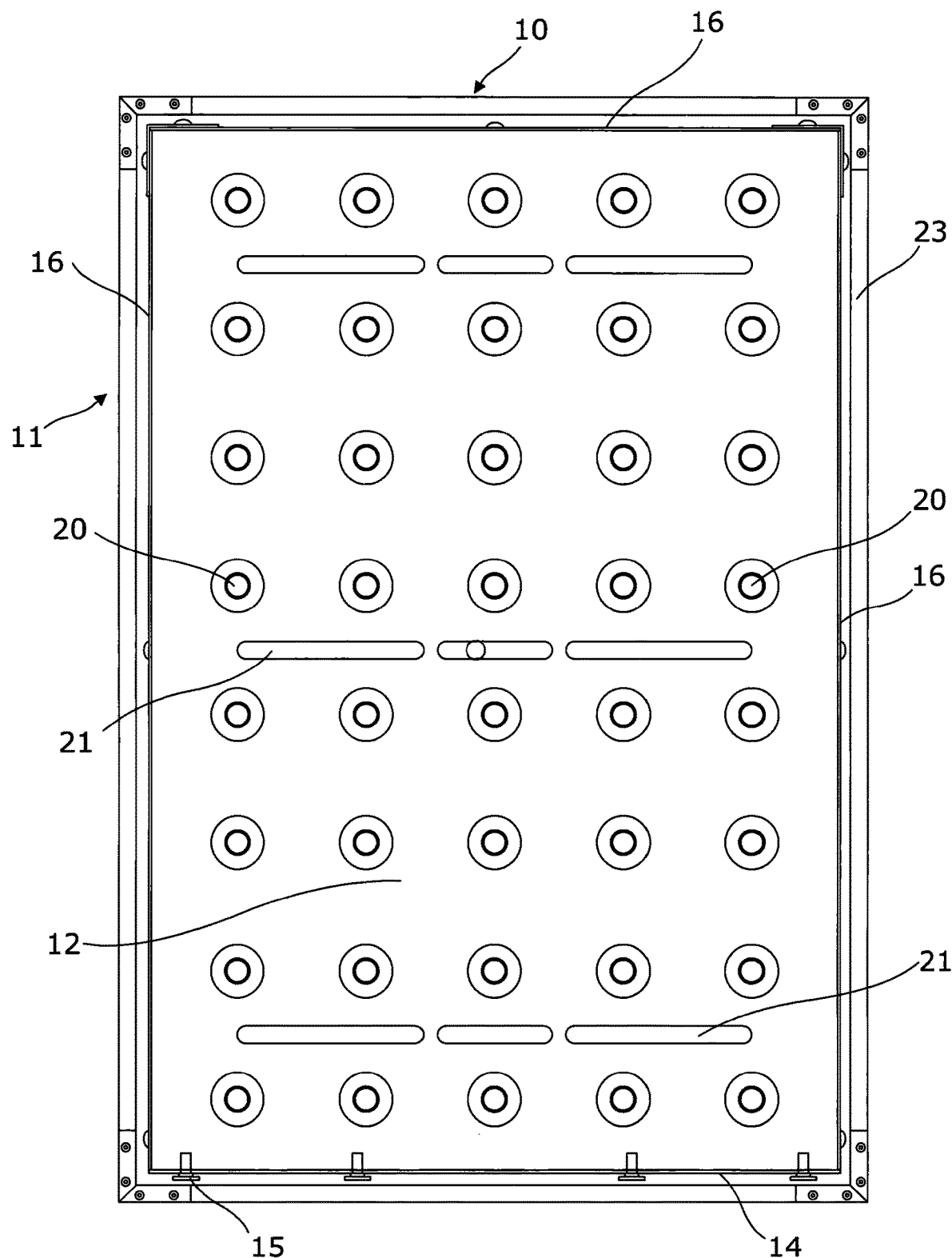
FIG. 8 is a plan view of the platform shown in FIG. 7.
Figure 9:
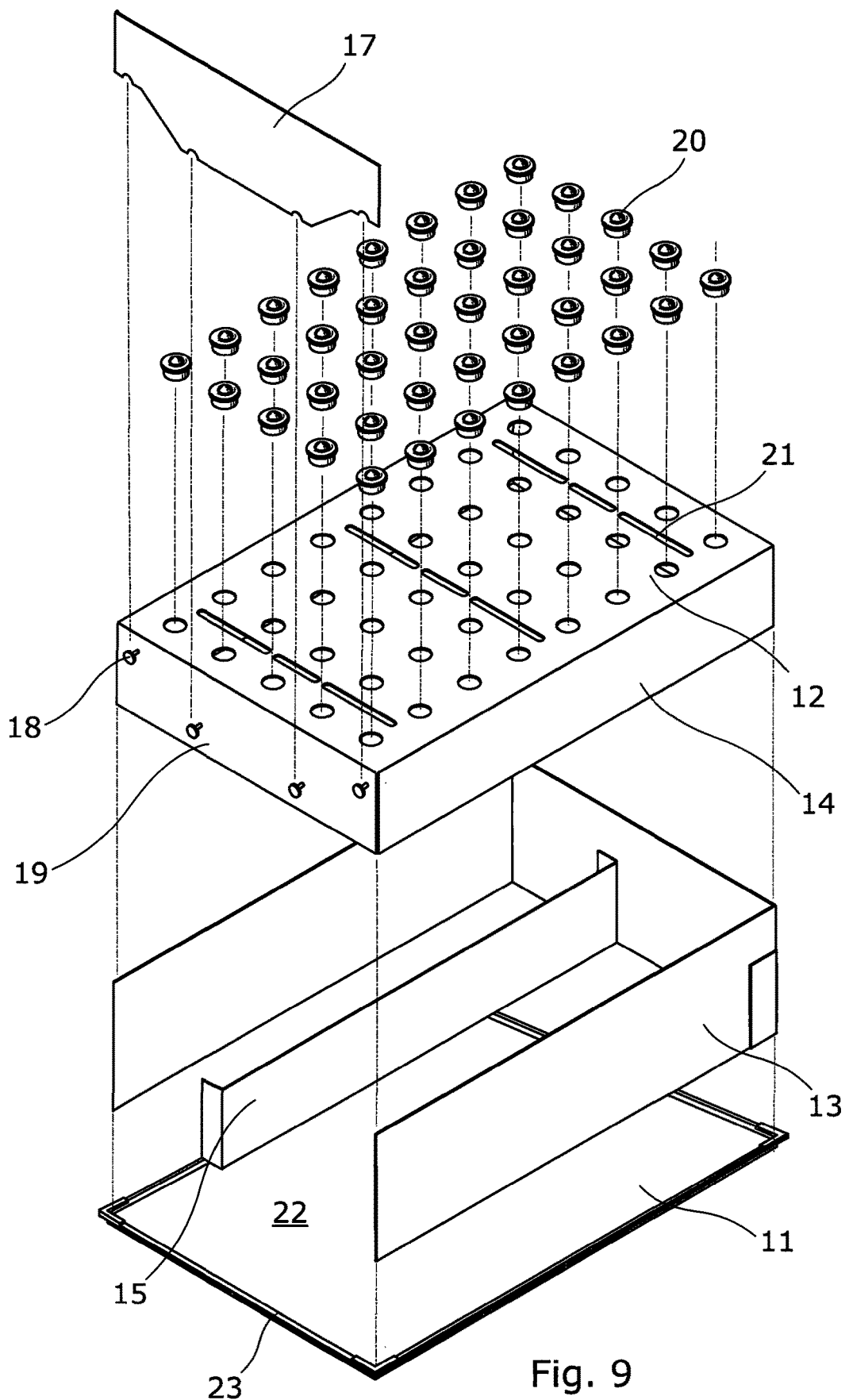
FIG. 9 is an exploded view of the platform shown in FIGS. 7 and 8.
Figure 10:
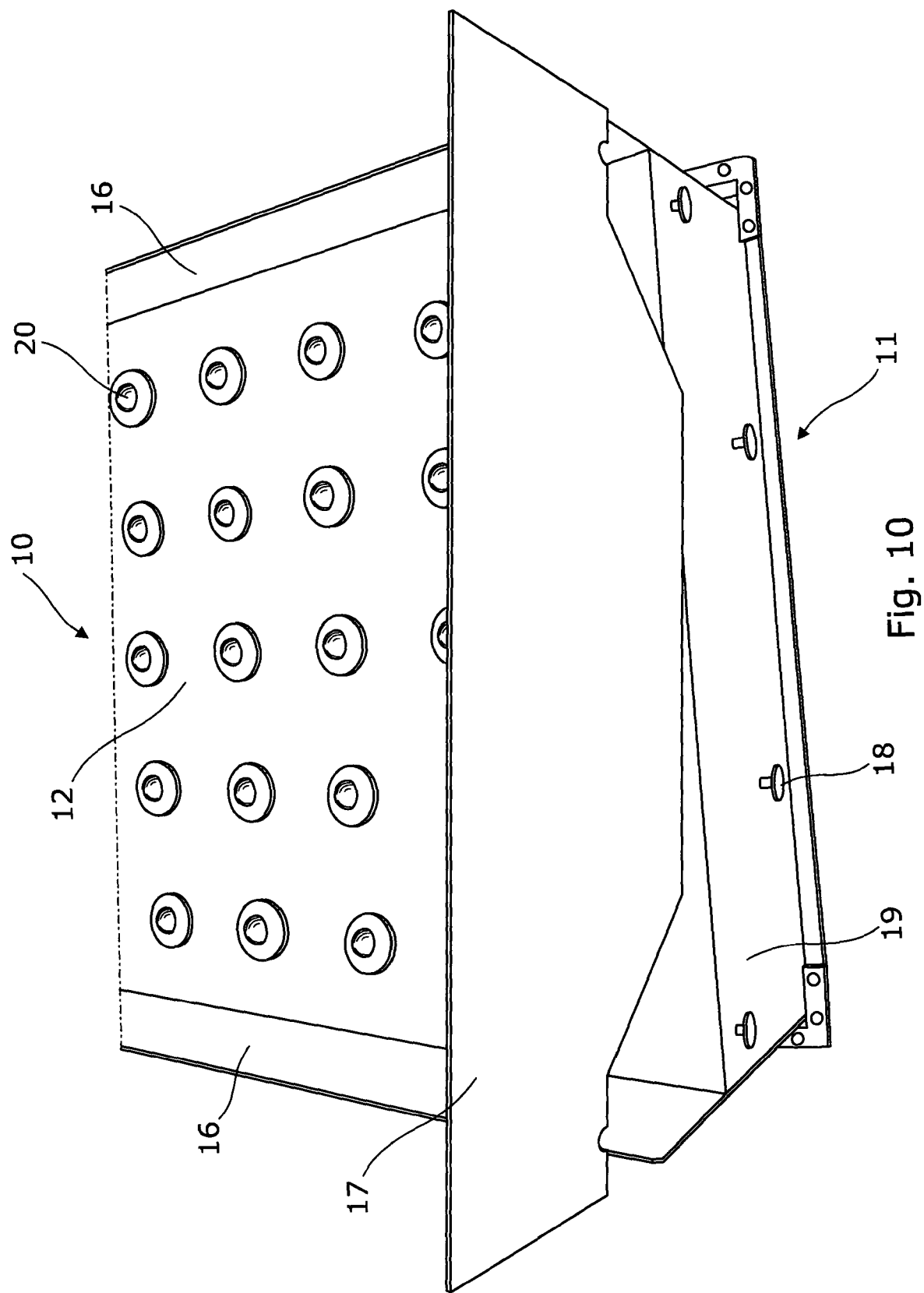
FIG. 10 is a view from above of one end of the platform shown in FIGS. 7 to 9.

At the side of the cabinet 1 is a door 24 through which an article A to be washed can be introduced into and removed from the washing apparatus 1. As shown in FIG. 2, the platform 10 locates inside the cabinet 1 of the washing apparatus so that the flange 19 to which the detachable plate 17 is attached faces the door 24. This enables heavy articles A to be located on the platform 10 easily and to be slid on to and off the platform 10 by means of the rollers 20. Also, in appropriate cases, the platform 10 as a whole or just the support plate 12 and frame 13 along with an article A can be inserted or removed from the cabinet 1 to facilitate handling and transportation of the article A to and from the washing apparatus as mentioned above.

The cabinet 1 and the washing apparatus 1 as a whole will now be described in more detail.

In addition to the door 24, the glove isolation cabinet 1 is provided with a viewing window 25 with one or more wipers 26 and a pair of rubber gloves 30 that project into the cabinet 1 to enable an operator to manipulate and manually wash an article within the cabinet 1. The washing liquid used is usually water. Hence, the washing apparatus may be plumbed into a mains water supply or use washing liquid, again typically water, recycled from the tank 6. An on/off switch 31 in a foot pedal starts and stops operation of a ventilation fan 32 and a pump 33, which are both located in the electrical compartment 7. The fan 32 is used to ventilate the compartment 7 during use in view of the heat-generating electrical equipment that it contains. The pump 33 acts to pump washing liquid from the tank 6 to the cabinet 1. This pump 33 may be omitted if the apparatus is supplied from a mains water supply but in either case, the washing liquid is discharged into the cabinet 1 via a hose 34 with a liquid-discharging nozzle 35. The nozzle 35 is interchangeable with other nozzles (not shown) provided in the cabinet 2 to provide appropriately shaped jets either for removing large areas of support material from an article A or for cleansing delicate and/or complex areas of the article. An adjustable pressure control knob 36 is connected to a pressure control valve (not shown) located upstream of the hose 34 in order that the pressure of the washing liquid can be controlled. The pressure control knob 36 enables an operator to vary the pressure of washing liquid supplied to the nozzle 35 during use of the apparatus as appropriate. The on/off switch 31 may also control operation of the wiper or wipers 26 and one or more lamps 37 that illuminate the interior of the cabinet 2 but in a modified arrangement these can be provided with their own separate on/off switches (not shown).

In a modified arrangement, a heater may be provided for the washing liquid. In addition, the cabinet 1 can be provided with a supply of compressed air, which may also be heated, that can be used to dry articles A after washing.

As the cabinet 1 is sealed during use, it is also provided at a top corner with a covered ventilation aperture which allows air out of the cabinet 1 but which is constructed such that washing liquid and any particles it contains cannot escape. Preferably, the ventilation aperture is adapted for connection to a fan with a HEPA filter.

At the bottom of the cabinet 2 is a drain 38, closable by a removable plug 39, that allows washing liquid to flow into the first filtration arrangement 4 housed in the drawer 3 via hose 40. Preferably, the bottom of the cabinet 2 is shaped so that liquid contained therein naturally flows towards the drain 38 and may be adapted to accommodate the tray 11 on a raised part thereof so that washing liquid that cascades over the edge 23 of the tray 11 flows towards the drain 38. The first filter arrangement 4 comprises a filter basket 41 that is covered by a removable filter bag 42, preferably made of woven plastics such as polypropylene, which can retain and filter out solid material down to a size of at least 25 µm and preferably down to around 0.5 µm. One or more disposable filter mats 43 may also be provided in the base of the basket 41 in addition to the bag 42. These mats 43 can be more easily removed and replaced after each washing operation than the filter bag 42. The drawer 3 provides easy access to the filter basket 41 and enables the removable filter bag 42 and the mats 43 to be replaced as required. Washing liquid flows through the basket 41 under the influence of gravity and collects in the drawer 5. The drawer 5 is provided with a float switch 44 that automatically turns on a pump 45 located in the compartment 7 once the level of liquid in the drawer 3 reaches the level of the float switch 44. The pump 45 pumps the washing liquid out of the drawer 3 via a weir plug 46 over which the washing liquid must flow in order to be pumped out of the drawer 3 by the pump 45. The weir plug 46 ensures that any large or heavy pieces of solid material that have slopped out of the filter arrangement 4 remain in the drawer 3 as the washing liquid is only pumped out of the drawer 3 until the liquid level has reduced to the upper level of the weir plug 46. Hence, in use at least the lower part of the basket 41 and the mats 43 are submerged in the washing liquid as the weir plug 46 is made of a sufficient size to ensure this is the case. These filtered-out residues remain submerged in liquid in the drawer 3 both during operation of the apparatus and after washing operations when the apparatus is opened to remove the article A and to replace any of the filters 42, 43. This ensures that the residues cannot become airborne. The weir plug 46 can be detached from the drawer 3 to allow the liquid in the drawer 3 to drain but this is under the control of the operator, who can take appropriate precautions.

The pump 45 pumps the washing liquid from the drawer 3 to and through the second filter arrangement 5, which comprises at least one and preferably a bank of three filter cartridges 47, 48, 49 that successively filter out solid material from the washing liquid of smaller and smaller size down to around a size of 1.0 µm in size. The first cartridge 47 comprises a filter capable of filtering out solid material equal to or greater than 25 µm in size. The second cartridge 48 filters out solid material equal to or greater than 10 µm in size and the third cartridge 49 filters out solid material equal to or greater than 5 µm in size. Once it has passed through the second filter arrangement 5, the washing liquid is collected in the tank 6 for reuse or, if mains water is being used as the supply, for discharge into a mains drain. It will be appreciated that the collection tank 6 acts as a holding tank so that any further solid material in the liquid it contains can also settle out at the bottom of the tank 6. Periodically, therefore, the tank 6 can be emptied and this material recovered.

As the washing liquid is collected in the tank 6 and constantly reused it is important that it does not become contaminated by harmful microorganisms and that biofilms are not allowed to develop in the tank 6. An ultra violet light sterilizer is therefore provided. A first sterilizer 50 may be provided within the cupboard 2 for periodic use within the tank 6 to prevent biofilms from building up. A second ultra violet light sterilizer (not shown) may also be provided as part of the pipework returning the washing liquid from the second filter arrangement 5 to the tank 6 to sterilize the washing liquid directly. This sterilizer may be switched on whenever the pump 45 is activated.

In use, a newly printed 3D-article, in particular an SML or an SLS printed article A, is located on the support plate 12 within the cabinet 1 through the door 24. The detachable plate 17 is located in position and the door 24 is then closed. The main on/off switch 9 may then be switched on and closure of the door 24 triggers a further switch (not shown), which with allows the switch 31 in the foot pedal to be also turned on. By using the rubber gloves 30, an operator can then jet wash the article A with washing liquid using the various nozzles 35 provided to remove loose solid material such as metal powder from the article A. The rollers 20 in the support plate 12 enable the operator to move and turn the article A so that all of its surfaces can be washed and so that washing liquid can be jetted into all interstices where loose powder may have collected in order to wash this powder out.

The spent washing liquid and washed-out powder runs off the article on to the support plate 12. The metal powder, being heavy, tends to collect on the plate 12 and may be trapped by a mat located thereon but in any event the upstand or upstands 16 and detachable plate 17 prevent it and the washing liquid from cascading off the edges of the plate 12 and ensure that any powder caught in the flow of washing liquid drains through the perforations 21 into the tray 11. Once in the tray 11, the powder predominantly tends to settle out on any mat covering the plate 22 of the tray 11 whereas the washing liquid once it has filled the tray 11 cascades over the raised edge 23 of the tray 11 into the base of the cabinet 1. It has been found that the platform 10 comprising the support plate 12, frame 13 and tray 11 captures most of the recoverable power. However, there is always a proportion that is not captured. This runs with the washing liquid through the drain 38 into the first filter arrangement 4. The filter bag 42 and the filter mat or mats 43 in the filter basket 41 filter out powder down to around 0.5 µm in size. However, there is always some spillage out of the basket 41 into the drawer 3. It will be appreciated, however, that all of the powder remains wet and submerged within the liquid retained in the drawer 3. Once the level of the liquid in the drawer 3 reaches the level of the float switch 44 then the pump 45 is automatically switched on to pump the liquid from the drawer 3 to the second filter arrangement 5 and thence into the tank 6 as described above. Liquid up to the level of the top of the weir plug 44 is, however, retained in the drawer 3. In the second filter arrangement, the filter cartridges 47, 48, 49 capture particles down to around 1.0 µm and smaller particles tend to settle out in the tank 6. If the washing liquid is water, then the water in the tank 6 is sufficiently clean for it to be emptied into a mains sewerage system when it is no longer required for reuse in the cabinet 1. All of the remaining filtered-out particulate material can be recovered from the platform 10, the tray 11, the filter arrangements 4 and 5 and from the tank 6 for safe disposal or for recycling and possible reuse. After washing, the cleaned article A can be taken out of the cabinet 1 and after drying is ready for use as required.

Hence the washing apparatus prevents metal powders from polluting the environment and keeps them wet so that they cannot become an explosion hazard. It also enables expensive heavy metal powders to be recovered The combination of a gravity feed through the first filter arrangement 4 and a pumped feed through the second filter arrangement 5 is highly effective at removing all bar the minutest metal particles. In addition, the platform 10 has a dual purpose. Not only does it assist an operator in the manipulation of a heavy article during a washing procedure, it also enables a large proportion of the washed off solid material such as metal powders to be readily recovered without the need to backwash filters such as the filter bag 41, the filter mats 42 and the filters in the cartridges 47, 48 and 49.

Although the washing apparatus of the present invention has been designed with the removal of metal powders from printed articles, it will be appreciated that can also be used for the removal of powders used in other 3-D printing methods, such as plastics powders, which are typically nylon powders.

The invention claimed is:

1. A washing apparatus for a 3D-printed article for removing support material from the article comprising:
   a glove isolation cabinet provided with a liquid-discharging nozzle to enable an operator to spray an article located in the cabinet with a washing liquid and a drain;
   a first filter arrangement that receives washing liquid discharged from the cabinet via the drain and through which the washing liquid drains under the influence of gravity;
   a first pump; and
   a second filter arrangement comprising at least one filter cartridge through which liquid that has passed through the first filter arrangement is pumped by the first pump;
   characterised in that the first filter arrangement is located in a trough in which washing liquid that has passed through the first filter arrangement accumulates whereby, in use, one or more filters of the filter arrangement are submerged to ensure filtered-out residue remains submerged in liquid, wherein the trough comprises a weir plug over which the washing liquid flows in order to be pumped out of the trough by the first pump.

2. A washing apparatus as claimed in claim 1, wherein said at least one filter cartridge is adapted to filter out solid material equal to or greater than 25 μm in size.

3. An apparatus as claimed in claim 1, wherein a float switch is located in the trough and is operationally linked to the first pump whereby the first pump is automatically switched on when the level of washing liquid in the trough reaches a level causing operation of the float switch.

4. An apparatus as claimed in claim 1, wherein the first filter arrangement is provided with at least one removable filter that can filter out solid material equal to or greater than 0.5 μm in size.

5. An apparatus as claimed in claim 1, wherein the second filter arrangement comprises at least first and second filter cartridges in series, which filter cartridges are collectively adapted to filter out solid material equal to or greater than 10 μm in size.

6. An apparatus as claimed in claim 5, wherein the second filter arrangement comprises a third filter cartridge that is in series with the first and second filter cartridges and that is adapted to filter out solid material equal to or greater than 5 μm in size.

7. An apparatus as claimed in claim 1, wherein washing liquid that has passed through the first and second filter arrangements is collected in a collection tank for reuse.

8. An apparatus as claimed in claim 7, comprising at least one ultra violet light sterilizer adapted to sterilize washing liquid in the collection tank and/or washing liquid that is be collected in the collection tank.

9. An apparatus as claimed in claim 8, wherein a second pump is provided to pump washing liquid from the collection tank to the liquid-discharging nozzle.

10. An apparatus as claimed in claim 1, wherein a platform is provided within the glove isolation cabinet on which an article to be washed is located, the platform comprising a tray above which is mounted a support plate on which the article sits.

11. An apparatus as claimed in claim 10, wherein the tray comprises a flat plate with a raised edge forming a weir over which the washing liquid can cascade but which predominantly retains solid particles in the tray.

12. An apparatus as claimed in claim 11, wherein the flat plate of the tray is covered by a mat.

13. An apparatus as claimed in claim 10, wherein a plurality of rollers is mounted in the support plate whereby the article is movable over the support plate.

14. An apparatus as claimed in claim 10, wherein the support plate defines at least one perforation through which washing liquid drains into the tray.

15. A platform as claimed in claim 10, wherein the support plate is surrounded by an upstand at least part of which is removably mounted allowing an article to be slid off or on to the support surface.

* * * * *